(12) United States Patent
Gennari et al.

(10) Patent No.: US 8,951,294 B2
(45) Date of Patent: Feb. 10, 2015

(54) SPINAL IMPLANT WITH A LOCKABLE BALL JOINT

(75) Inventors: Jean-Marie Gennari, Marseilles (FR); Herve Chataigner, Boussieres (FR); Jean-Marc Vital, Bordeaux (FR); Laurent Nogues, St Pierre-Reunion (FR); Hugues-Pascal Mousselard, Paris (FR); Pascal Kouyoumdjian, Nimes (FR); Jean-Michel Taillet, Marseilles (FR); Philippe Tisserand, Cabestany (FR)

(73) Assignee: Euros, La Ciotat (FR)

( * ) Notice: Subject to any disclaimer, the term of this patent is extended or adjusted under 35 U.S.C. 154(b) by 551 days.

(21) Appl. No.: 13/202,031

(22) PCT Filed: Feb. 19, 2010

(86) PCT No.: PCT/FR2010/000142
§ 371 (c)(1),
(2), (4) Date: Oct. 27, 2011

(87) PCT Pub. No.: WO2010/103198
PCT Pub. Date: Sep. 16, 2010

(65) Prior Publication Data
US 2012/0046701 A1    Feb. 23, 2012

(30) Foreign Application Priority Data

Mar. 12, 2009  (FR) .................................... 09 01138

(51) Int. Cl.
*A61B 17/86* (2006.01)
*A61B 17/70* (2006.01)
*A61B 17/88* (2006.01)

(52) U.S. Cl.
CPC ......... *A61B 17/7037* (2013.01); *A61B 17/7076* (2013.01); *A61B 17/7032* (2013.01); *A61B 17/8875* (2013.01)

USPC ............................ 606/308; 606/266; 606/267

(58) Field of Classification Search
USPC .................................. 606/266, 287, 300–321
See application file for complete search history.

(56) References Cited

U.S. PATENT DOCUMENTS

| 5,443,467 | A | 8/1995 | Biedermann et al. |
| 6,248,105 | B1 * | 6/2001 | Schlapfer et al. ............. 606/266 |

(Continued)

FOREIGN PATENT DOCUMENTS

| EP | 1 839 606 A1 | 10/2007 |
| WO | WO 2006116437 A2 * | 11/2006 |

OTHER PUBLICATIONS

International Search Report, dated Apr. 28, 2010, from corresponding PCT application.

*Primary Examiner* — Jerry Cumberledge
(74) *Attorney, Agent, or Firm* — Young & Thompson

(57) ABSTRACT

A spinal implant (100) includes an anchoring part (110) adapted to be anchored to a vertebra and having first connecting elements (112), and a mounting part (120) including both an internal axial housing (151) to receive transversely a connecting rod (30), this axial housing being terminated beside the anchoring part (110) by a bottom (156), and also second connecting elements that cooperate with the first connecting elements to form a ball-joint connection between the anchoring part and the mounting part. The spinal implant includes retaining elements that are situated near the bottom of the axial housing of the mounting part that are adapted to fasten a locking member in a stationary so-called locking position in which the ball-joint connection formed by the first and second connecting elements is locked to fasten the anchoring part and the mounting part in rotation relative to each other about at least two orthogonal axes.

14 Claims, 8 Drawing Sheets

(56) References Cited

U.S. PATENT DOCUMENTS

| | | |
|---|---|---|
| 6,254,602 B1 | 7/2001 | Justis |
| 6,485,491 B1 * | 11/2002 | Farris et al. .................... 606/250 |
| 7,087,057 B2 * | 8/2006 | Konieczynski et al. ...... 606/278 |
| 7,144,396 B2 * | 12/2006 | Shluzas ......................... 606/266 |
| 7,942,909 B2 * | 5/2011 | Hammill et al. .............. 606/267 |
| 8,221,472 B2 * | 7/2012 | Peterson et al. .............. 606/270 |
| 2006/0276791 A1 * | 12/2006 | Shluzas ............................ 606/61 |
| 2007/0055240 A1 * | 3/2007 | Matthis et al. .................. 606/61 |
| 2007/0288004 A1 | 12/2007 | Alvarez |
| 2008/0108992 A1 * | 5/2008 | Barry et al. ...................... 606/61 |
| 2008/0140136 A1 * | 6/2008 | Jackson ......................... 606/328 |
| 2009/0204155 A1 * | 8/2009 | Aschmann .................... 606/264 |
| 2013/0296946 A1 * | 11/2013 | Jackson ......................... 606/305 |

* cited by examiner

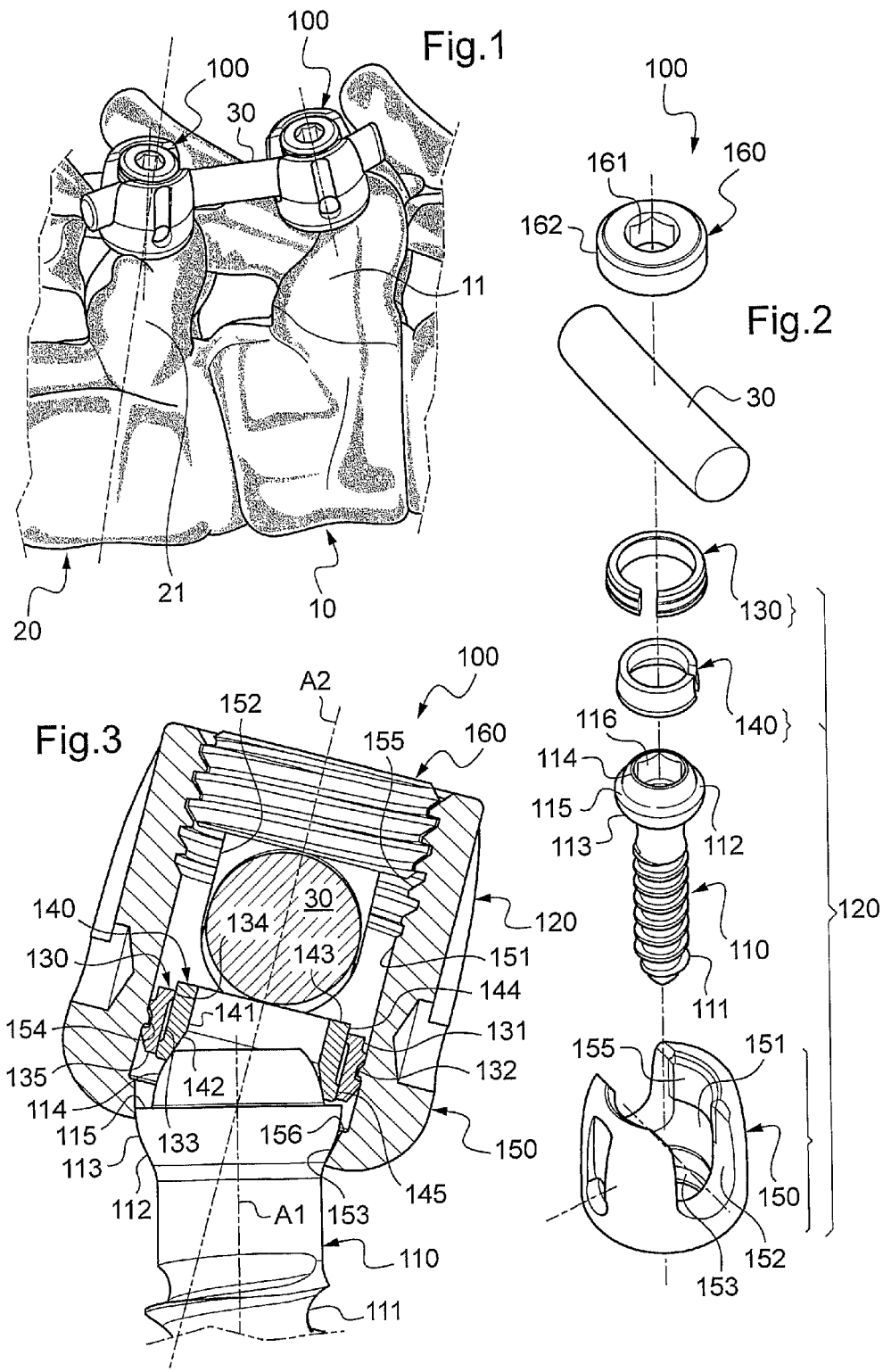

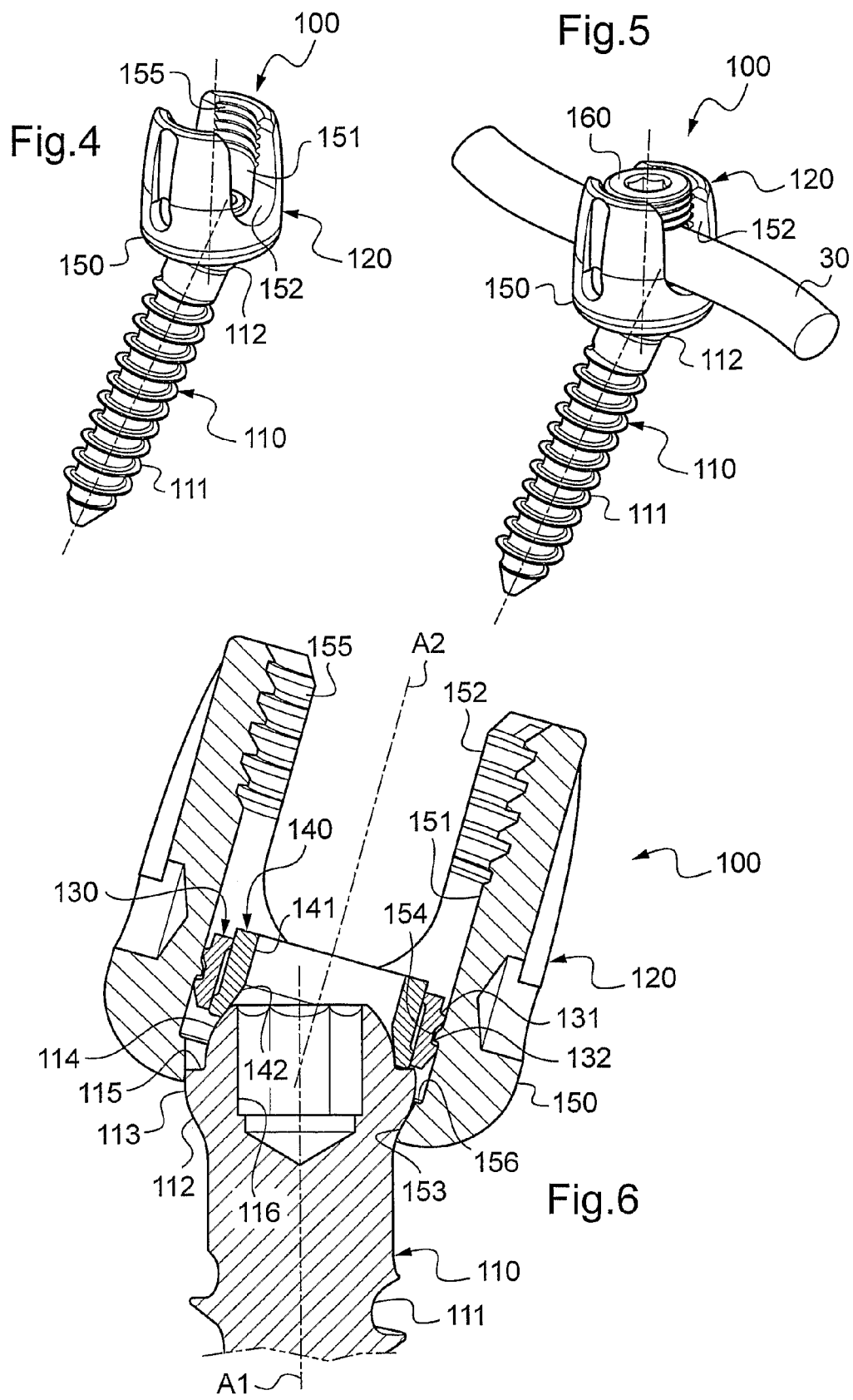

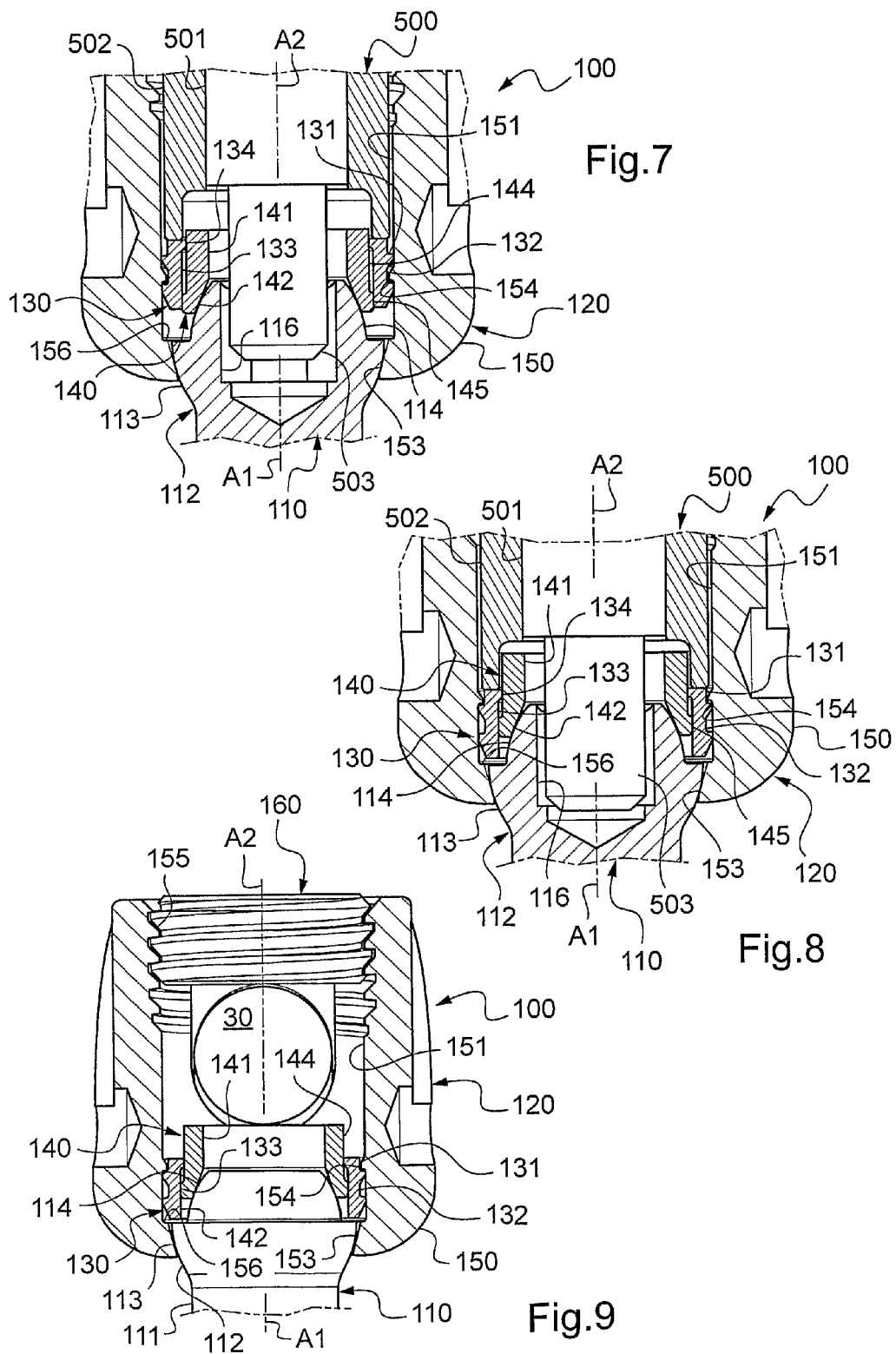

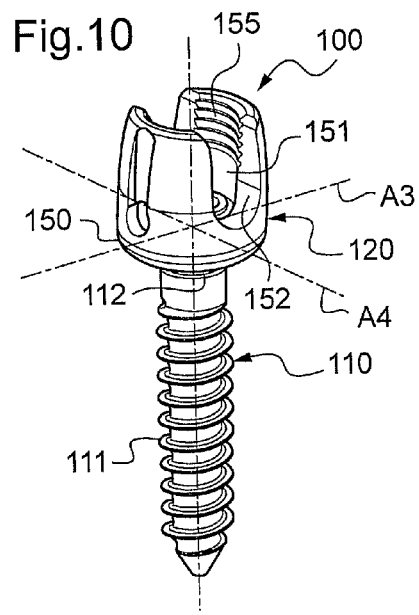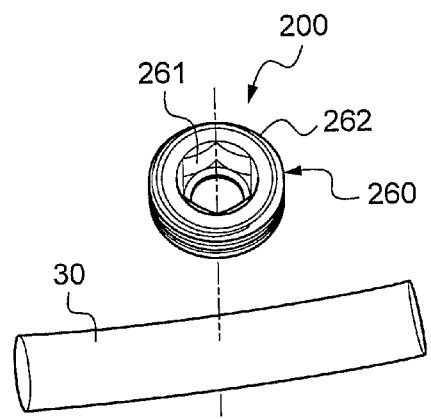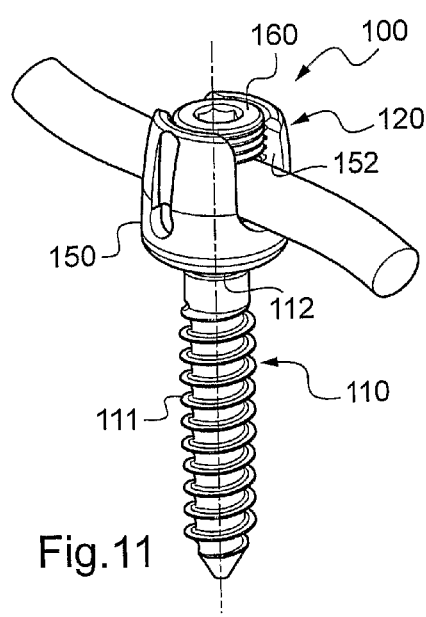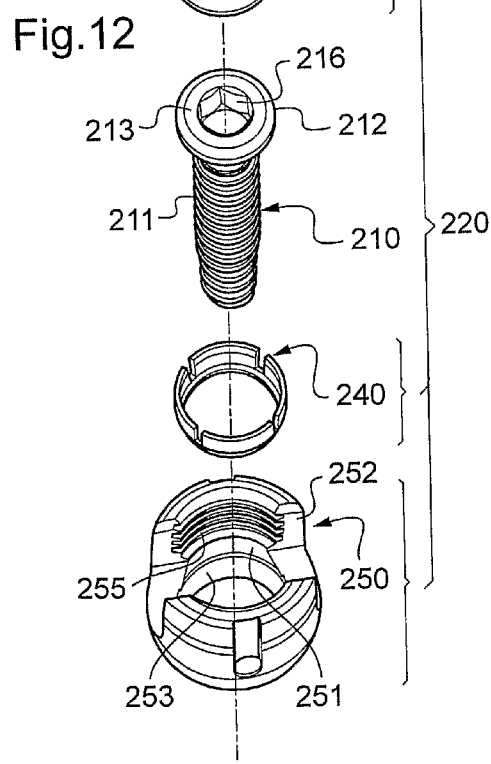

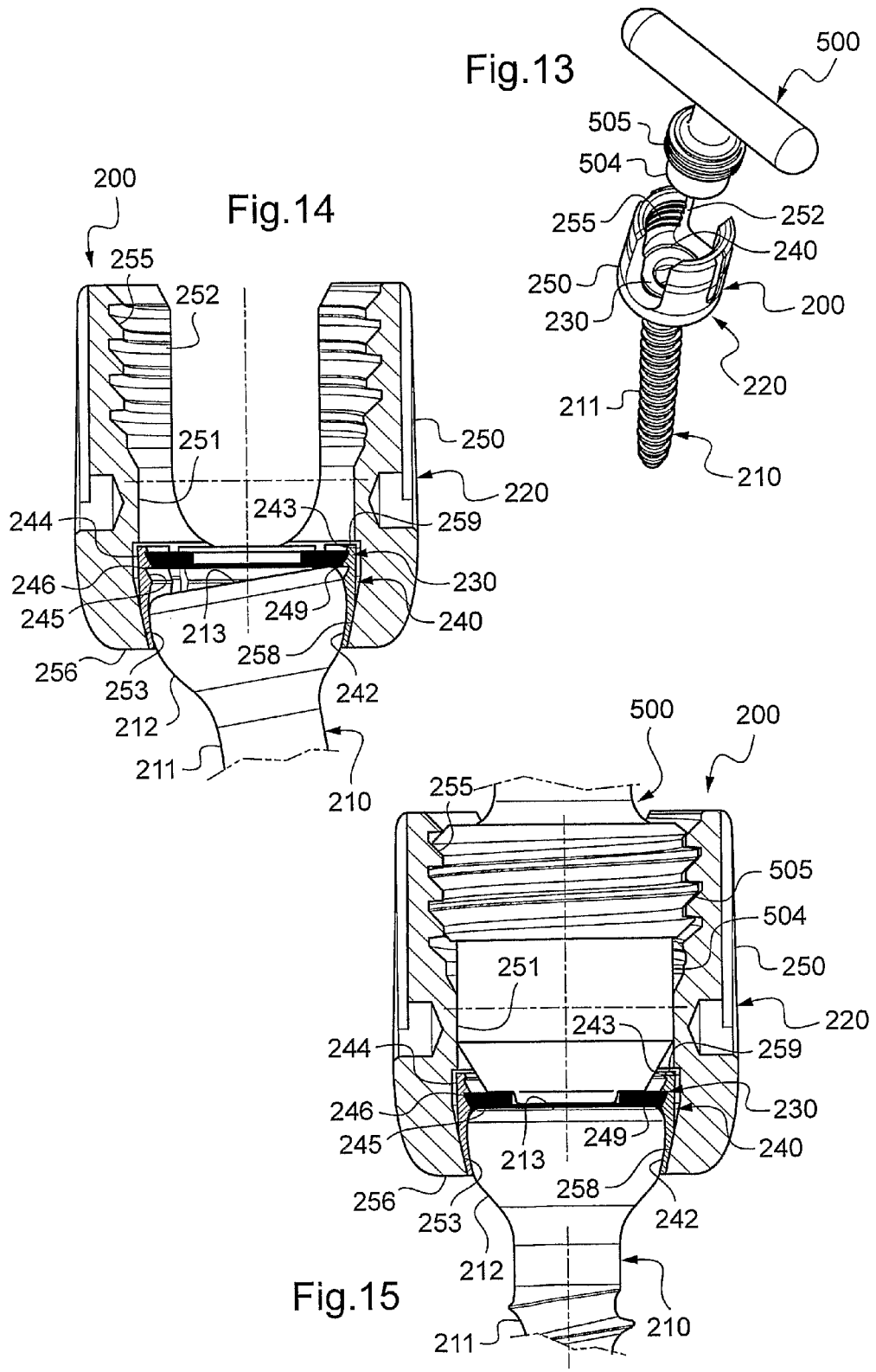

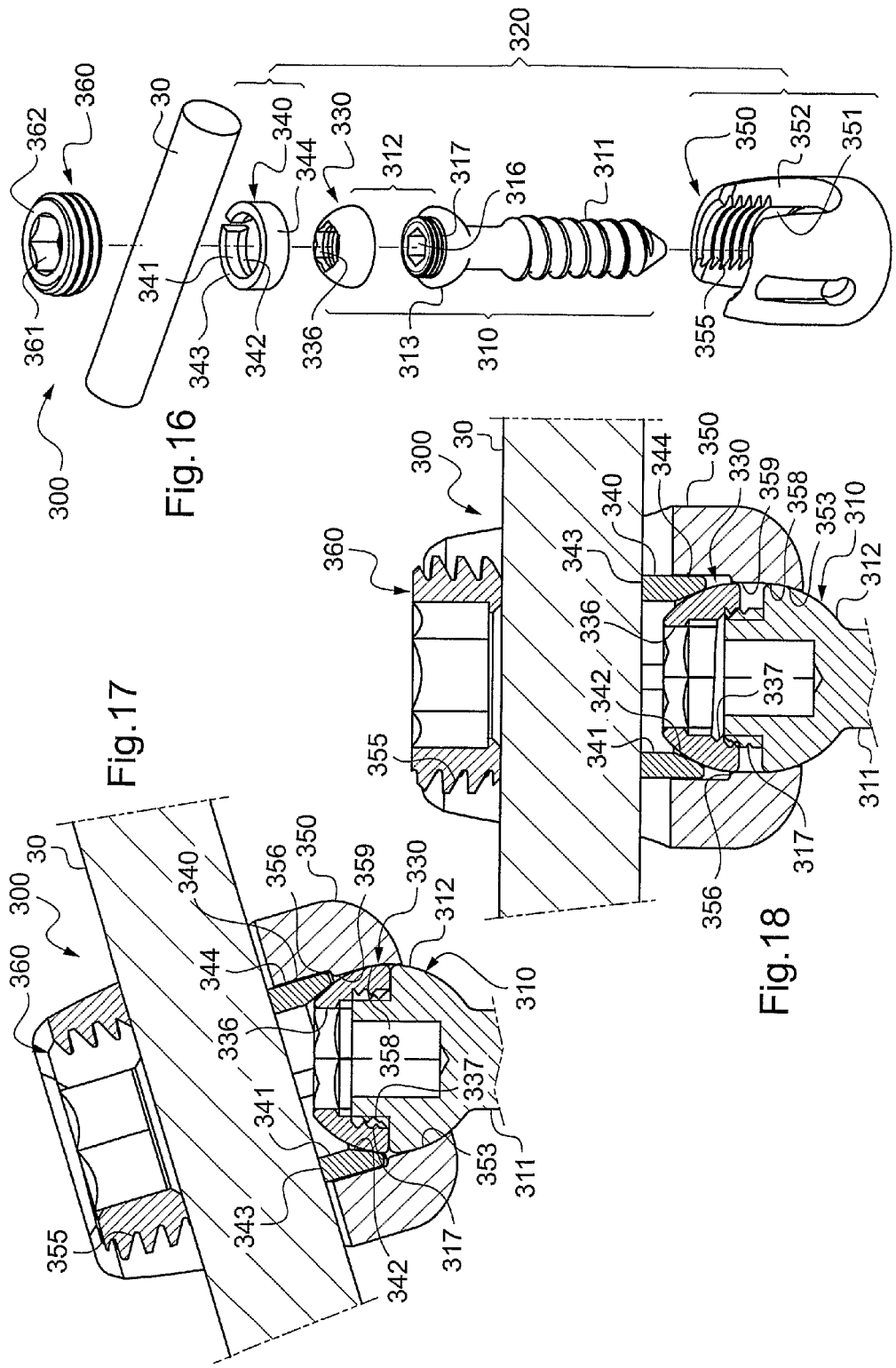

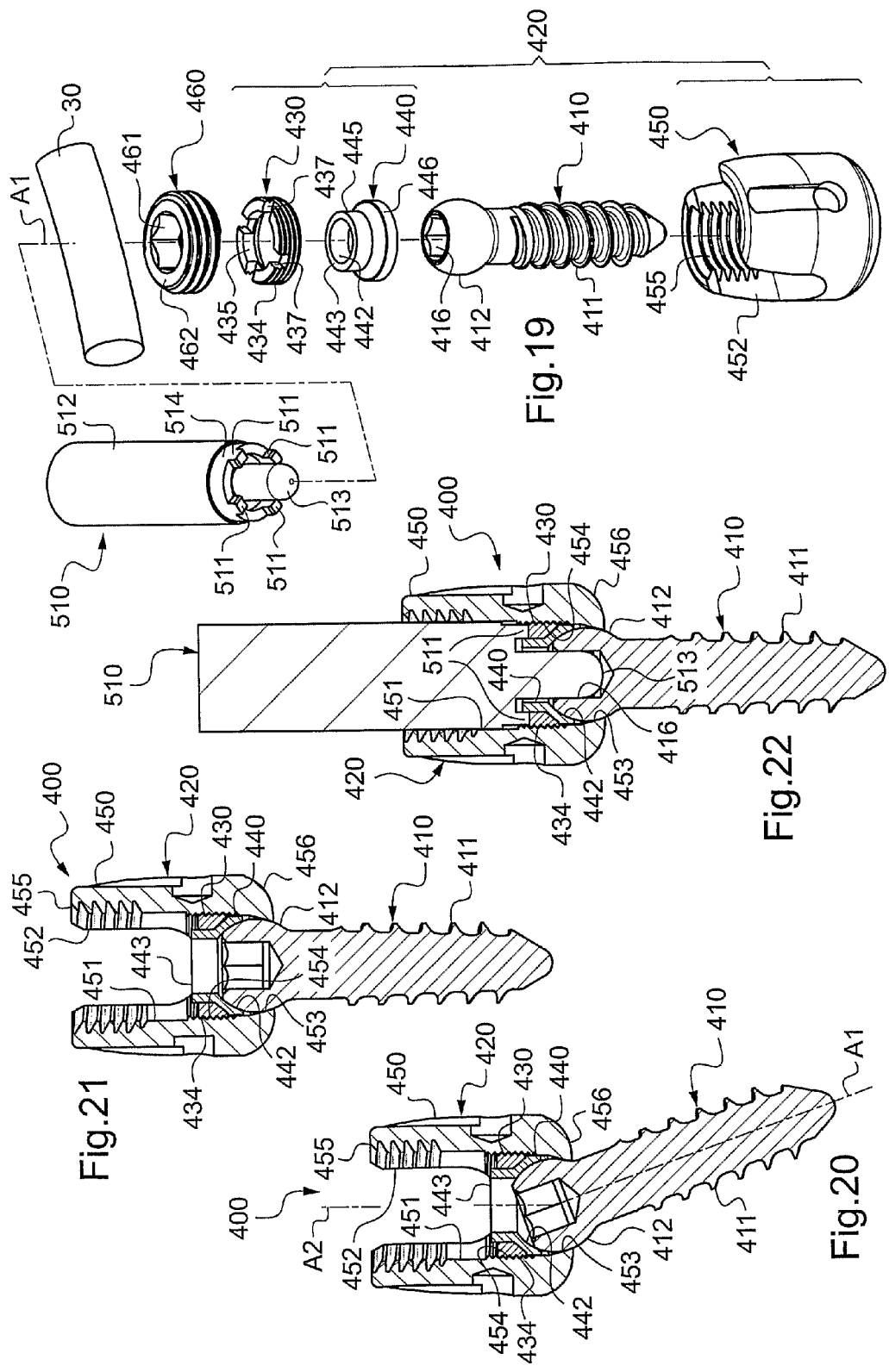

SPINAL IMPLANT WITH A LOCKABLE BALL JOINT

TECHNICAL FIELD TO WHICH THE INVENTION RELATES

The present invention relates generally to spinal implants intended to immobilize at least two vertebrae relative to each other.

It relates more particularly to a spinal implant including:
an anchoring part adapted to be anchored to a vertebra and including first connecting means; and
a mounting part comprising, both an internal axial housing open to the outside via two facing lateral openings in the form of cradles for receiving transversely a connecting rod, this axial housing being terminated beside the anchoring part by a bottom, and also second connecting means that cooperate with said first connecting means to form a ball-joint connection between said anchoring part and said mounting part.

TECHNOLOGICAL BACKGROUND

Spinal implants of the above-mentioned type are used in pairs and in combination with a connecting rod to treat arthrosis and vertebral fractures or to correct distortions of the vertebral column such as scoliosis or kyphosis.

To immobilize two vertebrae, a surgeon uses four spinal implants, two on each vertebra. To this end the surgeon engages the anchoring parts of the implants in the vertebrae and then fastens the implants of the two pairs together by means of two connecting rods, each of which extends from one vertebra to the other between the two implants. Those two connecting rods are bent beforehand as a function of the correction to be applied to the vertebral column. In that way the two rods are positioned parallel to the vertebral column to hold it substantially straight.

Two types of spinal implant are more particularly known in the art. Single-axis implants in which the anchoring part and the mounting part are aligned are known. In the majority of those implants, the anchoring part and the mounting part are stationary relative to each other and are formed as a single piece. Some of those single-axis implants are nevertheless such that their anchoring part and their mounting part are connected to each other by a pivot connection about the longitudinal axis of the implant.

Also known are multi-axis implants in which the anchoring part and the mounting part are connected to each other by a ball-joint connection.

Here the expression "ball-joint connection" refers to a connection that allows the mounting part to assume different inclinations relative to the axis of the anchoring part. The anchoring part and the mounting part are thus stationary in translation relative to each other along three axes in space but free to rotate about each of the three axes.

The expression "pivot connection" refers to a connection that allows the mounting part to turn about the anchoring part, remaining in alignment with its axis. The anchoring part and the mounting part are thus stationary in translation relative to each other along the three axes in space, stationary in rotation relative to each other about two of the three axes, and free to rotate about the axis of the anchoring part.

The surgeon may be called on to use one or the other of those two types of spinal implant, for example as a function of the trauma to be treated and the shape of the vertebral column of the patient.

There is a drawback in that the implant manufacturer must double the number of product lines to offer both types of spinal implant that surgeons need to operate on patients.

Surgeons for their part must manage stocks of the two types of implant and, before each operation, predict which type of spinal implant they are going to use.

One example of a multi-axis implant is described in Document EP 1 839 606. As described in that document, the implant includes:
a screw having a head that is part-spherical;
a tubular receiving part including at its bottom end an opening to receive the head of the screw;
a tubular pressure member engaged inside the receiving part so that its bottom end bears against the head of the screw, and its top end forms a cradle for receiving a connecting rod; and
a closure device comprising both an outer bolt screwed into the top end of the tubular receiving part in order to lock the pressure member against the head of the screw so as to prevent it from moving, and also an inner bolt screwed into the outer bolt to lock the connecting rod at the bottom of the cradle provided in the pressure member.

In the above document, the means for locking the ball-joint connection provided between the head of the screw and the receiving opening of the tubular receiving part are therefore situated above the receiving cradle of the connecting rod.

The drawback of the above implant is that the ball-joint connection can be locked only after the connecting rod has been engaged in the implant. Thus the surgeon is not able to lock it before operating on the patient.

There is also known from Document US 2007/0288004 a spinal implant including:
a screw including a part-spherical head;
a tubular tulip, defining internally an axial housing for receiving transversely a connecting rod and that has a threaded top part and a spherical bottom part;
a rosette that is adapted to be housed in the spherical bottom part of the tulip;
a locking member that is adapted to be screwed into the thread of the top part of the tulip to lock the connecting rod against the rosette, the effect of which is to compress the rosette in the spherical bottom part of the tulip and thus to prevent the screw from moving relative to the tulip.

The rosette has a stud adapted to be engaged in the socket in the head of the screw so that once the tulip is assembled to the screw the implant behaves as a single-axis implant. This rosette may moreover be replaced by a rosette with no stud so that the implant may behave as a multi-axis implant.

However, in the above document, the means enabling the head to pivot relative to the tulip and to lock the multi-axis function are carried by a single part, the rosette. Because of this, to change from a single-axis implant to a multi-axis implant, it is necessary to remove the whole of the rosette and therefore to dismantle the implant. Thus the surgeon is not able to lock the multi-axis function while operating on the patient.

OBJECT OF THE INVENTION

The object of the present invention is to propose a spinal implant able to provide a single-axis implant function and a multi-axis implant function in order to facilitate the work of the surgeon and to prevent duplication of the costs of manufacturing, storing, and managing the implants.

To this end, the invention proposes a spinal implant as defined in the introduction that includes retaining means that are situated in a space between the bottom of the cradles formed by the two lateral openings and the bottom of the axial housing of said mounting part and that are adapted to fasten a locking member separate from the second connecting means in a stationary so-called locking position in which the ball-joint connection formed by said first and second connecting means is locked to fasten said anchoring part and said mounting part in rotation relative to each other about at least two orthogonal axes.

Accordingly, by means of the invention, when the locking member is not in the locking position the implant behaves as a multi-axis implant. In contrast, when the locking member is in the locking position the implant behaves as a single-axis implant. Consequently, a single type of spinal implant enables the surgeon to treat all traumas of the vertebral column.

By means of the invention, the manufacturer and the surgeon need to manage only one spinal implant product line.

Moreover, the surgeon may choose which type of implant to fit to the vertebral column of the patient during the surgical operation itself, with the benefit of simplifying use of the implant.

In particular, the surgeon may configure the implant in the single-axis mode either before operating on the patient or during the operation. The surgeon may even configure it after engaging the anchoring part of the implant in the vertebral column of the patient. The surgeon may equally choose to preserve the multi-axis implant function and to prevent the ball-joint connection from moving only at the end of the operation, on engaging the connecting rod in the axial housing of the implant.

Other advantageous and non-limiting features of the spinal implant of the invention are as follows:

said retaining means are adapted to store a locking member in a stationary "storage" position that is separate from the locking position and in which the ball-joint connection formed by said first and second connecting means is left free;

when the ball-joint connection is locked, said anchoring part and said mounting part are stationary relative to each other;

when the ball-joint connection is locked, said anchoring part and said mounting part are free to pivot about a single main axis orthogonal to said two orthogonal axes;

said anchoring part includes a threaded body extending along a first axis, said axial housing extends along a second axis, and the retaining means are adapted to fasten said locking member in the locking position only when said second axis coincides with said first axis;

said first connecting means include a head that is at least partly spherical and said second connecting means include a ring with an inside face that bears against said head;

said axial housing is open to the outside via two facing lateral openings in the form of cradles and said ring has an end face that lies above the bottoms of the two lateral openings;

said axial housing is open to the outside at its end opposite from the bottom via an introduction opening and said mounting part includes near this introduction opening a thread that cooperates with a complementary thread of a locking screw to prevent said connecting rod and said ball-joint connection from moving;

a locking member is provided that is adapted to cooperate with said retaining means to be fastened in said locking position;

said locking member is part of said anchoring part;

the head of the anchoring part includes two parts screwed together, a first of which parts constitutes said locking member;

the bottom that terminates the axial housing beside the anchoring part has an opening through which said axial housing is open to the outside, this opening having a cylindrical part that lies over a spherical or conical part and said locking member, when it is in the locking position, is situated in contact with said cylindrical part of the opening;

said locking member is part of said mounting part;

said locking member is an annulus;

said locking member and said anchoring part include abutment faces which, when said locking member is in the locking position, are situated in contact with or in the immediate vicinity of each other;

said mounting means comprise a body that includes said bottom and defines said axial housing, said retaining means are formed integrally with the body, and said locking member has an outside face engaged in said retaining means;

said retaining means comprise a peripheral rib that extends into said axial housing, projecting from the inside face of the body that defines this axial housing;

said retaining means comprise a thread on the inside face of the body that defines said axial housing;

said mounting means include a ring engaged in said axial housing, said retaining means are formed integrally with said ring, and said locking member has an outside face engaged in said retaining means.

DETAILED DESCRIPTION OF AN EMBODIMENT

The following description with reference to the appended drawings, which is provided by way of non-limiting example, explains in what the invention consists and how it may be reduced to practice.

In the appended drawings:

FIG. 1 is a perspective view of two vertebrae locked relative to each other by means of a connecting rod and two spinal implants of the invention;

FIG. 2 is an exploded view of one of the spinal implants from FIG. 1 in a first embodiment of the invention;

FIG. 3 is a view in axial section of the spinal implant from FIG. 2, in which the ball-joint connection is left free;

FIGS. 4 and 5 are perspective views of the spinal implant from FIG. 3, alone and equipped with a locking screw for the connecting rod;

FIGS. 6 to 8 are diagrams showing the operation of locking the spinal implant from FIG. 2;

FIG. 9 is a view in axial section of the spinal implant from FIG. 2 in which the ball-joint connection is locked to provide a pivot connection;

FIGS. 10 and 11 are perspective views of the spinal implant from FIG. 9, alone and equipped with a locking screw for the connecting rod;

FIG. 12 is an exploded view of one of the spinal implants from FIG. 1 in a second embodiment of the invention;

FIG. 13 is a perspective view of the spinal implant from FIG. 12 and a locking tool;

FIG. 14 is a view in axial section of the spinal implant from FIG. 12 in which the ball-joint connection is left free;

FIG. 15 is a view in axial section of the spinal implant from FIG. 14 and the locking tool in which the ball-joint connection is locked to provide a pivot connection;

FIG. 16 is an exploded view of one of the spinal implants from FIG. 1 in a third embodiment of the invention;

FIG. 17 is a view in axial section of the spinal implant from FIG. 16 in which the ball-joint connection is left free;

FIG. 18 is a view in axial section of the spinal implant from FIG. 16 in which the ball-joint connection is locked to provide a pivot connection;

FIG. 19 is an exploded view of one of the spinal implants from FIG. 1 in a fourth embodiment of the invention;

FIG. 20 is a view in axial section of the spinal implant from FIG. 19 in which the ball-joint connection is left free;

FIG. 21 is a view in axial section of the spinal implant from FIG. 19 in which the ball-joint connection is locked to provide a pivot connection;

FIG. 22 is a view in axial section of the spinal implant from FIG. 19 and a locking tool for locking the ball-joint connection;

Figure 23:
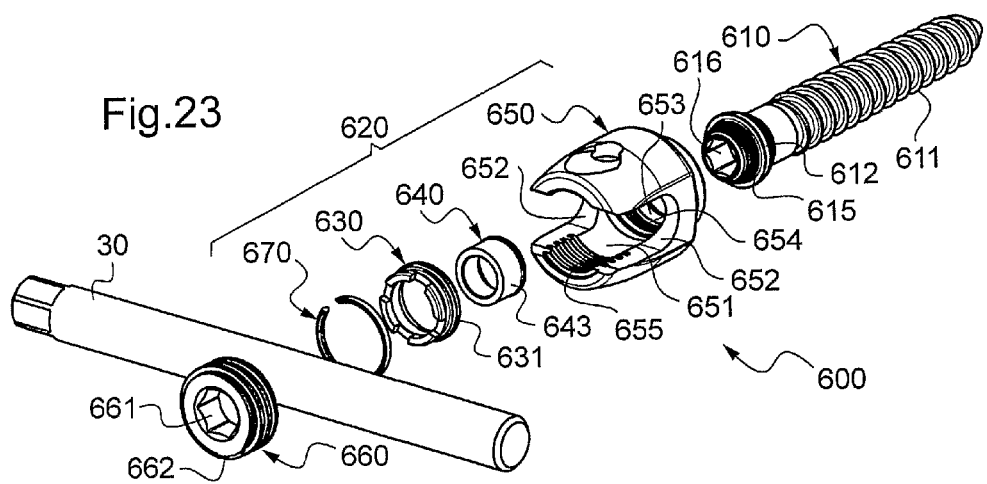
FIG. 23 is a diagrammatic exploded view of one of the spinal implants from FIG. 1 in a fifth embodiment of the invention.

Five spinal implants 100; 200; 300; 400; 600 are shown in FIGS. 2 to 11, 12 to 15, 16 to 18, 19 to 22, and 23 to 26, respectively.

As shown in these figures, the spinal implant 100; 200; 300; 400; 600 is a pedicular screw that includes an anchoring part 110; 210; 310; 410; 610 that is to be anchored by screwing into the pedicle 21, 11 of a vertebra 10, 20, and a mounting part 120; 220; 320; 420; 620 that is adapted to receive a connecting rod 30.

As FIG. 1 shows, this kind of connecting rod 30, when it extends between two spinal implants 100 anchored to two vertebrae 10, 20, enables those two vertebrae 10, to be prevented from moving relative to each other.

In the five spinal implants 100; 200; 300; 400; 600 (FIGS. 2, 12, 16, 19 and 23), the anchoring part 110; 210; 310; 410; 610 is in the form of a screw, with a threaded body 111; 211; 311; 411; 611 of axis A1 and, at the rear end of this threaded body, a head 112; 212; 312; 412; 612 having a socket 116; 216; 316; 416; 616 to receive the end of a driving tool. Here this receiving socket 116; 216; 316; 416; 616 is a hexagonal socket adapted to cooperate with an Allen key.

In these five implants, the mounting part 120; 220; 320; 420; 620 of the spinal implant 100; 200; 300; 400; 600 includes an elongate body 150; 250; 350; 450; 650 of generally cylindrical shape about an axis A2.

This body 150; 250; 350; 450; 650 defines internally an axial housing 151; 251; 351; 451; 651 that is a cylinder of circular cross-section about the axis A2. Beside the anchoring part 110; 210; 310; 410; 610 this axial housing is terminated by a bottom 156; 256; 356; 456; 656. This axial housing 151; 251; 351; 451; 651 is open to the outside at the rear of the spinal implant 100; 200; 300; 400; 600 via an introduction opening 155; 255; 355; 455; 655. It is also open towards the front via an opening 153; 253; 353; 453; 653 provided in the bottom 156; 256; 356; 456; 656 of the body, in which the head 112; 212; 312; 412; 612 of the anchoring part 110; 210; 310; 410; 610 is engaged.

The body 150; 250; 350; 450; 650 is further provided with two facing lateral openings 152; 252; 352; 452; 652 that extend lengthwise parallel to the axis A2 and that are open to the rear of the spinal implant 100; 200; 300; 400; 600. The bottoms of these lateral openings 152; 252; 352; 452; 652 that extend towards the front of the spinal implant 100; 200; 300; 400; 600 are rounded and thus cradle-shaped. These two lateral openings 152; 252; 352; 452; 652 enable the connecting rod 30 to be engaged transversely in the axial housing 151; 251; 351; 451; 651 of the body 150; 250; 350; 450; 650.

The spinal implant 100; 200; 300; 400; 600 further includes locking means 160; 260; 360; 460; 660 intended to cooperate with the body 150; 250; 350; 450; 650 to lock the connecting rod 30 in the body 150; 250; 350; 450; 650.

The locking means comprise a locking screw 160; 260; 360; 460; 660 having a threaded body 162; 262; 362; 462; 662 provided in its rear face that is accessible to the surgeon with a socket 161; 261; 361; 461; 661 for receiving the end of a driving tool. Here this receiving socket 161; 261; 361; 461; 661 is hexagonal and adapted to cooperate with an Allen key.

The threaded body 162; 262; 362; 462; 662 of this locking screw 160; 260; 360; 460; 660 is adapted to be screwed into a thread provided in the introduction opening 155; 255; 355; 455; 655 of the axial housing 151; 251; 351; 451; 651 of the body 150; 250; 350; 450; 650 of the mounting part 120; 220; 320; 420; 620.

When the locking screw 160; 260; 360; 460; 660 is screwed into this thread, it moves downwardly in the axial housing 151; 251; 351; 451; 651 and comes to bear against the connecting rod 30 in order to hold it stationary in the body 150; 250; 350; 450; 650 of the mounting part 120; 220; 320; 420; 620.

In the embodiments of the invention shown in the figures, as is described in more detail below, the anchoring part 110; 210; 310; 410; 610 and the mounting part 120; 220; 320; 420; 620 of the spinal implant 100; 200; 300; 400; 600 respectively comprise first and second connecting means that cooperate with each other so that the anchoring part and the mounting part are joined together by a ball-joint connection.

According to one particularly advantageous feature of the invention, the spinal implant 100; 200; 300; 400; 600 further comprises retaining means 154; 245; 317; 454; 654 situated near the bottom 156; 256; 356; 456; 656 of the body 150; 250; 350; 450; 650, which means are adapted to fasten a locking member 130; 230; 330; 430; 630 in a stationary "locking" position in which the ball-joint connection formed by said first and second connecting means is locked to render said anchoring part 110; 210; 310; 410; 610 and said mounting part 120; 220; 320; 420; 620 stationary in rotation relative to each other about at least one of two orthogonal axes A3, A4 (see FIG. 10).

The retaining means 154; 245; 317; 454; 654 are situated in a cradle-shaped space situated between the bottom 156; 256; 356; 456; 656 of the body 150; 250; 350; 450; 650 and the bottom of the lateral openings 152; 252; 352; 452; 652, this space including the bottom 156; 256; 356; 456; 656 of the body 150; 250; 350; 450; 650 itself and part of the axial housing 151; 251; 351; 451; 651.

Be this as it may, the retaining means 154; 245; 317; 454; 654 are situated so that the surgeon may have access to them and work on them independently of the connecting rod 30. The surgeon may therefore lock the ball-joint connection when so desired, either before operating on the patient or during the operation, before mounting the connecting rod 30 in the axial housing 151; 251; 351; 451; 651.

Here the retaining means 154; 245; 317; 454; 654 are more precisely situated between the bottom 156; 256; 356; 456; 656 of the body 150; 250; 350; 450; 650 and the bottoms of the lateral openings 152; 252; 352; 452; 652 of the body 150; 250; 350; 450; 650.

In the spinal implant 100; 200; 300 of the first three embodiments of the invention (FIGS. 1 to 18), locking the ball-joint transforms this ball-joint connection into a pivot connection. In this way, when the ball-joint connection is locked, the anchoring part 110; 210; 310 and the mounting part 120; 220; 320 are free to pivot about the same single axis A1, referred to as the main axis.

To be more precise, in these three embodiments of the invention the retaining means 154; 245; 317 are arranged so that they are able to fasten said locking member 130 in the locking position only if the axis A2 of the body 150; 250; 350; 450 coincides with the axis A1 of the anchoring part 110; 210; 310; 410 that constitutes said main axis.

In the spinal implant 400; 600 of the fourth and fifth embodiments of the invention (FIGS. 19 to 26), locking the ball-joint connection enables the anchoring part 410; 610 and the mounting part 420; 620 to be prevented from moving relative to each other. In the fourth embodiment of the invention the retaining means 454 are moreover able to fasten said locking member 430 in the locking position regardless of the orientation of the axis A2 relative to the axis A1. In contrast, in the fifth embodiment of the invention, the retaining means 654 are able to fasten said locking member 630 in the locking position only when the axis A2 of the body 650 coincides with the axis A1 of the anchoring part 610.

Accordingly, in each of these five embodiments of the invention, when no locking member is retained in the locking position by the retaining means 154; 245; 317; 454; 654, the implant 100; 200; 300; 400; 600 behaves as a multi-axial implant because the ball-joint connection is left free (the ball-joint connection is then referred to as activated—FIGS. 3, 14, 17, 20, and 25). In contrast, when the retaining means 154; 245; 317; 454; 654 fasten a locking member 130; 230; 330; 430; 630 in the locking position, the same implant 100; 200; 300; 400; 600 behaves as a single-axis implant because the ball-joint connection is either completely locked or locked to form a pivot connection (the ball-joint connection is then referred to as deactivated—FIGS. 9, 15, 18, 21, and 26).

The retaining means 154; 245; 317; 454; 654 are advantageously further adapted to store the locking member 130; 230; 330; 430; 630 in a stationary so-called storage position, separate from the locking position, in which the ball-joint connection is left active.

By means of the retaining means 154; 245; 317; 454; 654 the implant manufacturer may ship the spinal implant 100; 200; 300; 400; 600 with the locking member 130; 230; 330; 430; 630 locked in the storage position so that not only can it not be lost, but also it is easily accessible to the surgeon if it is desired to deactivate the ball-joint connection.

The first connecting means are preferably formed by the head 112; 212; 312; 412; 612 of the anchoring part 110; 210; 310; 410; 610 that is at least partly spherical to form the male member of the ball-joint connection.

The second connecting means for their part include a ring 140; 240; 340; 440; 640 that is housed in the axial housing 151; 251; 351; 451; 651 of the body 150; 250; 350; 450; 650 of the mounting part 120; 220; 320; 420; 620.

This ring 140; 240; 340; 440; 640 has an inside face 142; 242; 342; 442; 642 bearing against the head 112; 212; 312; 412; 612 of the anchoring part 110; 210; 310; 410; 610 to form at least part of the female member of the ball-joint connection.

The ring 140; 240; 340 is preferably split longitudinally over at least part of its length by at least one slot, which confers radial resilience on it so that it is able to adapt to the shape of the head 112; 212; 312 of the anchoring part 110; 210; 310.

The ring 140; 240; 340; 440; 640 has an end face 143; 243; 343; 443; 643 that lies to the rear of the bottoms of the cradles formed by the two lateral openings 152; 252; 352; 452; 652 of the body 150; 250; 350; 450; 650 of the mounting part 120; 220; 320; 420; 620. In other words, the ring 140; 240; 340; 440; 640 extends towards the introduction opening 155; 255; 355; 455; 655 of the axial housing 151; 251; 351; 451; 651 of the body 150; 250; 350; 450; 650 so that a very small portion of its length is situated between the introduction opening 155; 255; 355; 455; 655 and the bottoms of the two lateral openings 152; 252; 352; 452; 652 of the body 150; 250; 350; 450; 650.

Accordingly, when the surgeon tightens the locking screw 160; 260; 360; 460; 660 in the thread provided at the introduction opening 155; 255; 355; 455; 655 of the axial housing 151; 251; 351; 451; 651, this locking screw comes to bear on the connecting rod 30 that in turn bears on the rear face 143; 243; 343; 443; 643 of the ring 140; 240; 340; 440; 640, which locks movement of the ring relative to the head 112; 212; 312; 412; 612 of the anchoring part 110; 210; 310; 410; 610. Accordingly, this locking screw 160; 260; 360; 460; 660 enables the mounting part 120; 220; 320; 420; 620 to be prevented from moving relative to the anchoring part 110; 210; 310; 410; 610 so that the axis A2 has the required orientation relative to the axis A1.

In the spinal implant 100; 200; 400; 600 of the first, second, fourth, and fifth embodiments of the invention, shown in FIGS. 2 to 11, 12 to 15, 19 to 22, and 23 to 26, respectively, the locking member 130; 230; 430; 630 is part of the mounting part 120; 220; 420; 620.

To be more precise, it consists of an annulus housed in the axial housing 151; 251; 451; 651 of the body 150; 250; 450; 650 of the mounting part 120; 220; 420; 620 and, like all other components of the implant, it is made of titanium.

In the first, second, and fifth embodiments of the invention, the locking member 130; 230; 630 and the anchoring part 110; 210; 610 include abutment faces that, when said locking member 130; 230; 630 is in the locking position, are in contact with or in the immediate vicinity of each other, which deactivates the ball-joint connection.

To be more specific, in the first embodiment of the invention shown in FIGS. 2 to 11, the head 112 of the anchoring part 110 has two hemispherical parts 113, 114, comprising a front hemispherical part 113, the top of which is connected to the threaded body 111 of the anchoring part 110, and a rear hemispherical part 114, the top of which faces toward the mounting part 120. This rear hemispherical part 114 has a smaller diameter than the front hemispherical part 113. This difference in diameter between the two hemispherical parts 113, 114 generates on the head 112 of the anchoring part 110 an annular shoulder 115 about the axis A1.

In a corresponding manner, the opening 153 situated at the bottom of the axial housing 151 of the body 150 of the mounting part 120 has either a frustoconical shape or a part spherical (spherical segment) shape of the same diameter, ignoring clearance, as the front hemispherical part 113 of the head 112 of the anchoring part 110. This opening 153 thus forms part of said second connecting means. In other words, it forms part of the female member of the ball-joint connection.

As shown in FIG. 3, here the ring 140 has a substantially tubular shape with a cylindrical outside face 144 of circular cross-section about the axis A2 that is bordered at its front end by an outer crown 145 of greater diameter. The ring 140 also has an inside face in two parts, comprising a cylindrical rear part 141 of circular cross-section about the axis A2 and a frustoconical front part 142 engaged over the rear hemispherical part 114 of the head 112 of the anchoring part 110.

The locking member 130 has an annular shape and is engaged over the outside face 144 of the ring 140. It is to this end split longitudinally, which confers on it radial resilience to adapt to the outside diameter of the ring 140. The locking member 130 has a cylindrical inside face 133 of circular cross-section about the axis A2. It has an inside diameter equal, ignoring clearance, to the outside diameter of the crown 145 of the ring 140. It is bordered, at its rear end, by an inner crown 134. Thus it is adapted to side along the outside face 144 of the ring 140 as far as an abutment position in which its inner crown 134 comes into contact with the outer crown 145 of the ring 140.

In this embodiment of the invention, the retaining means 154 of the locking member 130 are formed with the body 150 of the mounting part 120. In this instance they are formed by a peripheral rib 154 that extends into the axial housing 151, projecting from the inside face of this axial housing 151, and that here is of circular symmetry about the axis A2.

The locking member 130 has on its outside face at least one corresponding peripheral groove 131, 132 to be engaged over said peripheral rib 154 to be fastened in a locking position.

As shown in the figures, the locking member 130 has two clips that define two circular peripheral grooves 131, 132 about the axis A2. These two peripheral grooves 131, 132 enable locking of the locking member 130 onto the peripheral rib 154 of the body 150, at will, either in a storage position (FIG. 3) or in a locking position (FIG. 9).

In the storage position, the front face 135 of the locking member 130 is situated at a distance from the annular shoulder 115 of the head 112 of the anchoring part 110 so as to leave the ball-joint connection activated.

In contrast, in the locking position, the front face 135 of the locking member 130 is situated in contact with or in the immediate vicinity of the annular shoulder 115 of the head 112 of the anchoring part 110 so as to deactivate the ball-joint connection. The front face 135 of the locking member 130 and the annular shoulder 115 of the head 112 of the anchoring part 110 thus form abutment faces, each of circular symmetry about the coinciding axes A1 and A2.

The expression "immediate vicinity" means that these two abutment faces are situated at a distance from each other such that they prevent movement of the mounting part 120 relative to the anchoring part 110 about an axis orthogonal to the main axis A1 of more than 5 degrees.

Here the peripheral rib 154 has a cross-section in the shape of a right-angle triangle having its hypotenuse facing the rear of the body 150 of the mounting part 120, so that the locking member 130 may be engaged in the inside of the axial housing 151 from the rear of the body 150, in the storage position and then the locking position, but can neither move from the locking position to the storage position nor be extracted from the body 150. It is thus held captive.

The spinal implant 100 is fitted to a vertebra 10, 20 by the surgeon in the following manner.

When the surgeon takes up a new spinal implant 100, it is preferably already equipped both with a locking member 130 disposed in the storage position and also with a locking screw 160 screwed into the body 150 of the mounting part 120.

The surgeon then begins by extracting this locking screw 160 from the body 150. Having access to the receiving socket 116 in the head 112 of the anchoring part 110 of the implant 100, the surgeon screws this anchoring part 110 into the vertebrae 10, 20 of the patient.

The surgeon then decides whether or not it is necessary to deactivate the ball-joint connection of the spinal implant 100 to provide the best support for the vertebral column of the patient.

If the ball-joint connection is to be left active (FIGS. 4 and 6), then the previously bent to shape connecting rod 30 is placed in the axial housing 151 of the body 150 of the mounting part 120 through the lateral openings 152 (FIG. 5). Whilst holding the connecting rod 30 in place, for example using forceps, the surgeon then screws the locking screw 160 into the thread of the introduction opening 155 of the body 150.

The surgeon then tightens the locking screw 160 so that the connecting rod 30 comes to bear on the ring 140 in order to prevent the ball-joint connection from moving.

In contrast, if the surgeon wishes to deactivate the ball-joint connection before fitting the connecting rod 30, a locking tool 500 is used to move the locking member 130 from its storage position to its locking position.

As shown in FIGS. 7 to 9, this kind of locking tool 500 preferably has a cylindrical body 501, a cylindrical end 503 of smaller diameter adapted to be engaged in the receiving socket 116 of the head 112 of the anchoring part 110, and a tubular part 502 that extends around the cylindrical end 503 so as to be able to bear on the rear face of the locking member 130 without interfering with the ring 140.

Using this locking tool 500, the surgeon may firstly straighten up the mounting part 120 relative to the anchoring part 110 (FIG. 7) by engaging the cylindrical end 503 of the locking tool 500 in the receiving socket 116 in the head 112 of the anchoring part 110. The axes A1 and A2 therefore coincide with the main axis.

The surgeon may then push on the locking member 130 so that its first peripheral groove 132 is disengaged from the peripheral rib 154 of the body 150 and its second peripheral groove 131 in turn engages over said peripheral rib 154 (FIGS. 8 and 10). This operation is made possible by the slots in the locking member 130 and the ring 140 that enable these two members to be deformed elastically in the radial direction so that the locking member 130 can move from the storage position to the locking position. At this stage, the ball-joint connection is therefore deactivated, so that the anchoring part 110 and the mounting part 120 of the implant 100 are joined together by a pivot connection.

The surgeon then proceeds in a similar manner to fasten the connecting rod 30 by engaging it in the axial housing 151 of the body 150 and by screwing the locking screw 160 into the thread of the introduction opening 155 of the body 150 so as to prevent the pivot connection from moving (FIG. 11).

In the second embodiment of the invention shown in FIGS. 12 to 15, the head 212 of the anchoring part 210 has a hemispherical shape with its top connected to the threaded body 211 of the anchoring part 210 and its base 213 facing the rear of the mounting part 220. This base is plane with the exception of a central part in which there is a recess formed by said receiving socket 216.

In corresponding manner, the ring 240 has a substantially tubular shape with a cylindrical outside face 244 of substantially circular cross-section about the axis A2 and an inside face 242 in two parts, comprising a front part 248 receiving the head 212 of the anchoring part 210 and a rear part 249 receiving the locking member 230.

The front part 248 has a part-spherical shape with a diameter equal, ignoring clearance, to the diameter of the head 212 of the anchoring part 210. This front part 248 constitutes said second connecting means in the sense that it forms the female member of the ball-joint connection.

The ring 240 is housed in a housing that is formed by the opening 253 situated at the bottom of the axial housing 251 of the body 250 of the mounting part 220.

To be more precise, this opening 253 has a cylindrical rear part 259 of circular cross-section about the axis A2 that is extended by a frustoconical front part 358 having its top facing the anchoring part 210. By means of this frustoconical shape, when a connecting rod 30 bears on the rear face 243 of the ring 240, the ring moves downwardly in the opening 253 and is radially compressed onto the head 210 of the anchoring part, the effect of which is to prevent the ball-joint connection from moving.

In this embodiment of the invention, the means for retaining the locking member 230 in the locking position and in the storage position are formed with the ring 240. Here they are formed by peripheral grooves 245, 246 situated on the rear part 249 of the inside face 242 of the ring 240. These two main grooves 245, 246 are of circular symmetry about the axis A2 and of triangular cross-section.

The locking member 230 for its part has a flat washer shape with an inside diameter greater than the greatest dimension of the receiving socket 216 in the head 212 of the anchoring part 210 and an outside diameter equal, ignoring clearance, to the diameter of the peripheral grooves 245, 246 of the ring 240.

Thus the locking member 230 is adapted to be locked, at will, in the storage position in the rear peripheral groove 246 (FIG. 14) of the ring 240 or in the locking position in the front peripheral groove 245 (FIG. 15), without impeding insertion of an Allen key into the receiving socket 216 in the head 212 of the anchoring part 210.

Movement of the locking member 230 from one position to the other is made possible by the radial resilience of the ring 240, which is conferred on it by four slots that extend over part of its length and that are regularly distributed around its perimeter.

In the storage position, the front face of the locking member 230 is at a distance from the plane part of the base 213 of the head 212 of the anchoring part 210 so as to leave the ball-joint connection activated.

In contrast, in the locking position, the front face of the locking member 230 is situated in contact with the base 213 of the head 212 of the anchoring part 210 so as to deactivate the ball-joint connection so that the anchoring part 210 and the mounting part 220 of the implant 200 are connected to each other by a pivot connection.

Here the peripheral grooves 245, 246 have cross-sections in the shape of right-angle triangles with their hypotenuses facing the rear of the body 250 of the mounting part 220 so that the locking member 230 may be engaged inside the axial housing 251 from the rear of the body 250 into the storage position and then the locking position, but can neither move from the locking position to the storage position nor be extracted from the body 250. It is thus held captive.

As FIGS. 13 and 15 show, here the locking member 230 is also moved from its storage position to its locking position by means of a locking tool 500 adapted to come into contact with the rear face of the locking member 230.

As shown in FIG. 15, this locking tool 500 has a cylindrical body 504 provided with a thread 505 identical to the thread of the locking screw 260. It therefore suffices to screw this locking tool 500 into the thread of the introduction opening 255 of the axial housing 251 to move the locking member 230 from its storage position to its locking position. The force needed to move the locking member 230 is therefore reduced.

In the spinal implant 300 of the third embodiment of the invention shown in FIGS. 16 to 18 the locking member 330 is part of said anchoring part 310.

To be more specific, the head 312 of the anchoring part 310 includes two hemispherical parts 313, 330 that are screwed together, comprising a front hemispherical part 113 connected at the top to the threaded body 311 of the anchoring part 310 and a rear hemispherical part that constitutes said locking member 330.

To this end the base of the front hemispherical part 113 includes a threaded stud 317 having an end face that includes a recess forming a socket 316 for receiving an Allen key.

In corresponding manner the base of the locking member 330 includes a threaded bore 337 that is screwed onto this threaded stud 317. The top of this locking member 330 includes a recess forming a socket 336 for receiving an Allen key. As FIGS. 17 and 18 show, the threaded bore 337 and the receiving socket 336 communicate with each other here.

In this embodiment of the invention, the retaining means for the locking member 330 are formed with the anchoring part 310 by the threaded stud 317. They are adapted to fasten the locking member 330 in the storage position when it is screwed in until it abuts against the threaded stud 317 or in the locking position when it is partially unscrewed from the threaded stud 317.

In corresponding manner, the opening 353 situated at the bottom of the axial housing 351 of the body 350 has a cylindrical rear part 359 of circular cross-section about the axis A2 that lies over a front part 358 of part-spherical shape having a diameter equal, ignoring clearance, to the diameter of the front hemispherical part 313 of the head 312 of the anchoring part 310.

The front part 358 of the opening 353 is thus part of said second connecting means in the sense that it constitutes part of the female member of the ball-joint connection.

The rear part 359 of the opening 353 for its part enables deactivation of this ball-joint connection when the locking member 330 is partially unscrewed from the threaded stud 317 (FIG. 18) so that the anchoring part 310 and the mounting part 320 of the implant 300 are connected to each other by a pivot connection.

In this position, the circular outlines of the bases of the two hemispherical parts 313, 330 of the head 312 of the anchoring part 310 lie within the cylindrical rear part 359 of the opening 353, which locks the ball-joint connection to provide the pivot connection.

As shown in FIG. 16, the ring 340 has a substantially tubular shape, here with a cylindrical outside face 344 of circular cross-section about the axis A2, and of the same diameter, ignoring clearance, as the axial housing 351. It has a two-part inside face comprising a cylindrical rear part 341 of circular cross-section about this axis A2 and a frustoconical front part 342 engaged over the locking member 330.

The surgeon fits the spinal implant 300 to a vertebra 10, 20 in the following manner.

After extracting the locking screw 360 from the body 350 of the mounting part 320, the surgeon has access to the receiving socket 316 in the head 312 of the anchoring part 310 of the implant 300 and screws this anchoring part 310 into the vertebra 10, 20 of the patient.

The surgeon then decides whether or not to deactivate the ball-joint connection of the spinal implant 300.

If the ball-joint connection is to be left active (FIG. 17), then the locking member 330 is screwed in until it abuts against the threaded stud 317 in the storage position. The previously bent to shape connecting rod 30 is then placed in the axial housing 351 of the body 350 via the lateral openings 352. The locking screw 360 is then screwed into the thread of the introduction opening 355 of the body 350 and this locking screw 360 is tightened so that the connecting rod 30 comes to bear on the ring 340 and thus prevents the ball-joint connection from moving.

In contrast, if the surgeon wishes to deactivate the ball-joint connection, then an Allen key is used merely to move the locking member 330 from its storage position to its locking position.

To this end the surgeon unscrews the locking member 330 over part of the length of the threaded stud 317 (FIG. 18) so that the locking member 330 is for the most part inside the axial housing 351 near the bottoms of the lateral openings 352 of the body 350. In this way the head 312 of the anchoring part 310 is locked to provide a pivot connection relative to the mounting part 320.

The surgeon then proceeds in exactly the same manner to fasten the connecting rod 30 by engaging it in the axial housing 351 and by screwing the locking screw 360 into the thread of the introduction opening 355 of the body 350 to prevent the pivot connection from moving (FIG. 11).

In the fourth embodiment of the invention shown in FIGS. 19 to 22, the head 412 of the anchoring part 410 is spherical and is engaged in the opening 453 provided in the bottom 456 of the body 450. It is held in this opening 453 by the ring 440.

To this end the ring 440 has two parts, comprising a tubular rear part 445 against which the connecting rod 30 comes to bear and a frustoconical front part 446 that is adapted to bear on the head 412 of the anchoring part 410. To be more precise, the inside face of the front part 446 of the ring 440 has a part-spherical shape of the same diameter, ignoring clearance, as the head 412 of the anchoring part 410. This front part 446 of the ring 440 is then part of said second connecting means in the sense that it forms part of the female member of the ball-joint connection.

The ring 440 is housed in the axial housing 451 in the vicinity of the bottom 456 of the body 450 of the mounting part 420.

In this embodiment of the invention, the means 454 for retaining the locking member 430 in the locking and storage positions is formed with the body 450. In this instance they are formed by a thread 454 that extends over the cylindrical inside face of the axial housing 451 from the rear edge of the opening 453 in the bottom 456 of the body 450 toward the engagement opening 455 of the body 450.

The locking member 430 has for its part a ring shape with an inside diameter greater than the greatest dimension of the receiving socket 416 in the head 412 of the anchoring part 410 and an outside diameter slightly less than the diameter of the axial housing 451. The outside face of this locking member 430 is provided with a thread 434 enabling a locking member 430 to be screwed into the thread 454 provided in the axial housing 451 near the bottom 456 of the body 450.

The inside face of this locking member 430 has a cylindrical rear part 435 of circular cross-section about the axis A2 of the same diameter as the tubular rear part 445 of the ring 440 and a frustoconical front part 436 adapted to be pressed against the outside face of the frustoconical front part 446 of the ring 440.

The locking member 230 is thus adapted to be screwed into the thread 454 of the axial housing 451, sliding along the tubular rear part 445 of the ring 440, so as to be locked at will in the storage position (FIG. 20) or the locking position (FIG. 21).

In the storage position, the locking member 430 is screwed into the thread 454 of the axial housing 451 with a low tightening torque so as to leave the ball-joint connection activated. The surgeon can thus incline the axis A2 of the body 450 of the mounting part 420 relative to the axis A1 of the anchoring part 410 at will.

In contrast, in the locking position, the locking member 430 is screwed into the thread 454 of the axial housing 451 with a high tightening torque so as to deactivate the ball-joint connection. In this position, the anchoring part 410 and the mounting part 420 of the implant 400 are prevented from moving relative to each other.

As shown in FIG. 21, the anchoring part 410 and the mounting part 420 are locked in an aligned position (the axes A1 and A2 coincide). Alternatively, the surgeon may prevent the anchoring part 410 and the mounting part 420 from moving so that they are held in a mutually inclined position.

To facilitate screwing the locking member 430 into the thread 454 of the axial housing 451, this locking member 430 has four recessed notches 437 in its rear face regularly distributed around its perimeter.

The locking tool 510 (FIGS. 19 and 22) used to screw in the locking element 430 includes in corresponding relationship a cylindrical body 512 having a diameter less than the diameter of the axial housing 451 and equipped at its front end with a peripheral crown 514 provided with four lugs 511 adapted to be engaged in the notches 437 of the locking member 430.

Here this locking tool 510 is equipped with a front stud 513 of smaller diameter that is situated at the center of the peripheral ring 514 and that ensures that the ball-joint connection is locked only when the anchoring part 410 and the mounting part 420 of the implant 400 are aligned.

Using this locking tool 510, the surgeon may initially straighten up the mounting part 420 of the implant 400 relative to its anchoring part 410 by engaging the front stud 513 of the locking tool 510 in the receiving socket 416 in the head 412 of the anchoring part 410.

The surgeon can then screw in the locking member 430 by engaging the lugs 511 of the locking tool 510 in the notches 437 of the locking member 430 and turning the locking tool 510 until the ring 440 is locked against the head 412 of the anchoring part 410 in order to prevent the ball-joint connection from moving.

Alternatively, the locking tool may equally have no front stud. The locking tool could then equally be used to lock the ball-joint connection in a position in which the anchoring part 410 and the mounting part 420 of the implant 400 are inclined relative to each other.

In the fifth embodiment of the invention shown in FIGS. 23 to 26, the head 612 of the anchoring part 610 has two hemispherical parts with different diameters to define between them an annular shoulder 615 about the axis A1. Here these two hemispherical parts are grooved to increase their adhesion.

In a corresponding manner, the opening 653 situated at the bottom of the axial housing 651 of the body 650 of the mounting part 620 has a part-spherical shape to form the female member of the ball-joint connector.

Figure 25:
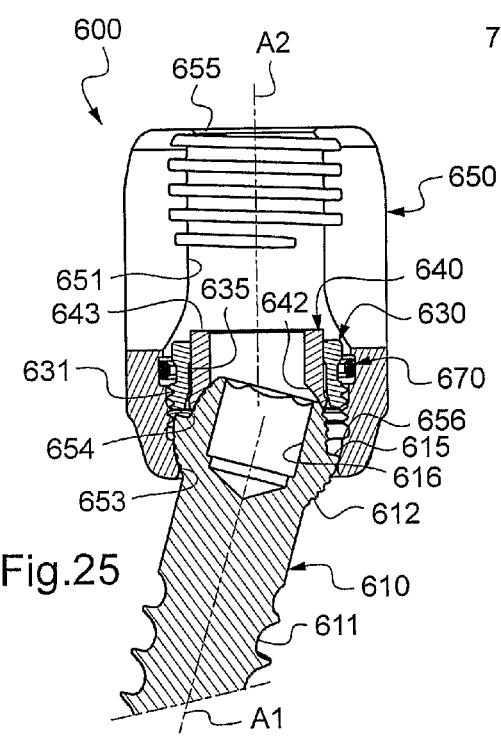
FIG. 25 is a view in axial section of the spinal implant from FIG. 23 in which the ball-joint connection is left free.
Figure 26:
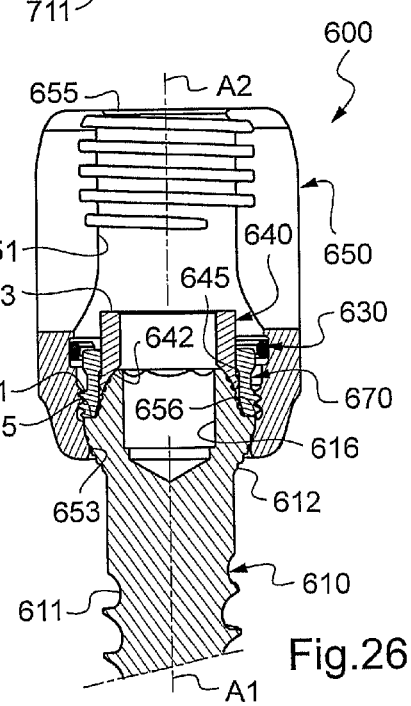
FIG. 26 is a view in axial section of the spinal implant from FIG. 23 in which the ball-joint connection is locked.

As shown in FIG. 25, the ring 640 has a substantially tubular shape. It is bordered at its front end by an outer ring. Internally, at its front end, it has a spherical part 642 engaged over the rear hemispherical part of the head 612 of the anchoring part 610.

The locking member 630 for its part has an annular shape. Internally, at its rear end, it has a groove 635 with an inside diameter, ignoring clearance, equal to the outside diameter of the ring 640. This locking member 630 may thus be threaded over the ring 640 so that it is able to slide along the outside face of the ring 640 as far as an abutment position in which its screw 635 comes into contact with the outer crown of the ring 640.

In this embodiment of the invention, the retaining means 654 of the locking member 630 are formed with the body 650 of the mounting part 620. In this instance they include a thread that lies inside the axial housing 651.

In corresponding manner, and on its outside face, the locking member 630 has a thread 631 adapted to be screwed into the thread 654 of the body 650.

As shown in the figures, the retaining means 654 for the locking member 630 further include to the rear of the thread a peripheral groove that accommodates a circlip 670 for retaining the locking member 630 in the axial housing 651 of the body 650. Here this circlip is formed by a simple split ring.

This circlip 670 therefore allows the locking member 630 to be locked in the storage position (FIG. 25) when the thread 631 of the locking member 630 is unscrewed from the thread of the body 650. In this storage position, the front face of the locking member 630 is situated at a distance from the annular shoulder 615 of the head 612 of the anchoring part 610 so as to leave the ball-joint connection activated.

In contrast, in the locking position, when the locking member 630 is screwed into the thread 654 of the body 650, the front face of the locking member 630 is in contact with the annular shoulder 615 of the head 612 of the anchoring part 610 so as to deactivate the ball-joint connection. In this position, the body 650 is held in a stationary position relative to the anchoring part 610.

Figure 24:
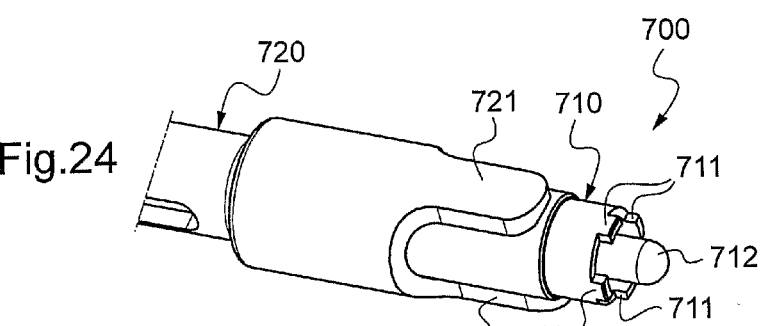
FIG. 24 is a diagrammatic perspective view of a locking tool for the spinal implant from FIG. 23.

The spinal implant 600 is fitted to a vertebra 10, by the surgeon using a locking tool 700 of the type shown in FIG. 24.

Here the locking tool 700 includes an inner rod 710 mounted so as to be movable in rotation in an outer tube 720.

The outer tube 720 includes at its front end two lateral extensions 721 of shape complementary to the shape of the lateral openings 652 of the body 650. Thus, during installation of the spinal implant 600 on a vertebra 10, 20, this outer tube 720 allows the body 650 of the implant to be held in the stationary position relative to the vertebrae.

The inner rod 710 for its part includes four lugs 711 in the shape of upstanding crenellations on its front end adapted to be engaged in notches in corresponding relationship on the rear end of the locking member 630. Thus, during installation of the spinal implant 600 on a vertebra 10, 20, this inner rod 710 allows the locking member 630 to be screwed into the bore of the body 650 of the implant so as to place the locking member 630 in the locking position.

This inner rod 710 is furthermore equipped with a front stud 712 enabling the mounting part 620 to be aligned on the axis of the anchoring part 610 of the spinal implant 600 before the locking member 630 prevents the ball-joint connection from moving.

The invention claimed is:

1. A spinal implant comprising:
an anchoring part adapted to be anchored to a vertebra and including a threaded body extending along a first axis and a first connecting means;
a mounting part comprising both an internal axial housing extends along a second axis and that is open to an outside of the spinal implant via two facing lateral openings in the form of cradles for receiving transversely a connecting rod, the axial housing being terminated beside the anchoring part by a bottom, and also second connecting means that cooperate with said first connecting means to form a ball-joint connection between said anchoring part and said mounting part;
retaining means that are adapted to fasten a locking member in a stationary locking position in which the ball-joint connection formed by said first and second connecting means is locked so that said anchoring part and said mounting part are locked from rotation relative to each other about at least two orthogonal axes;
wherein said retaining means are situated in a space between a bottom of the cradles formed by the two lateral openings and the bottom of the axial housing,
wherein said locking position is achieved only when said second axis coincides with said first axis, and
wherein the locking member is separate from the second connecting means.

2. A spinal implant according to claim 1, wherein said retaining means are adapted to store said locking member in a stationary storage position that is separate from the locking position and in which the ball-joint connection formed by said first and second connecting means is left free.

3. A spinal implant according to claim 1, wherein, when the ball-joint connection is locked, said anchoring part and said mounting part are stationary relative to each other.

4. A spinal implant according to claim 1, wherein, when the ball-joint connection is locked, said anchoring part and said mounting part are free to pivot about the first axis orthogonal to said at least two orthogonal axes.

5. A spinal implant according to claim 1, wherein said first connecting means include a head that is at least partly spherical and wherein said second connecting means include a ring with an inside face that bears against said head.

6. A spinal implant according to claim 5, wherein said axial housing is open to the outside of the spinal implant via two facing lateral openings in the form of cradles and wherein said ring has an end face that lies above the bottoms of the cradles formed by said two lateral openings.

7. A spinal implant according to claim 1, wherein said axial housing is open to the outside of the spinal implant at its end opposite from the bottom via an introduction opening and said mounting part includes near this introduction opening a thread that cooperates with a complementary thread of a locking screw to prevent said connecting rod and said ball-joint connection from moving.

8. A spinal implant according to claim 1, including a locking member adapted to cooperate with said retaining means to be fastened in said locking position.

9. A spinal implant according to claim 8, wherein said locking member is part of said anchoring part.

10. A spinal implant according to claim 9, wherein said first connecting means include a head that is at least partly spherical and wherein said second connecting means include a ring with an inside face that bears against said head, and the head of the anchoring part includes two parts screwed together, a first of which parts constitutes said locking member.

11. A spinal implant according to claim 10, wherein the bottom that terminates the axial housing beside the anchoring part has an opening through which said axial housing is open to the outside of the spinal implant, this opening having a cylindrical part that lies over a spherical or conical part, and wherein said locking member, when it is in the locking position, is situated in contact with said cylindrical part of the opening.

12. A spinal implant according to claim 8, wherein said locking member is part of said mounting part.

13. A spinal implant according to claim 12, wherein said locking member is an annulus.

14. A spinal implant according to claim 12, wherein said locking member and said anchoring part include abutment faces which, when said locking member is in the locking position, are situated in contact with or in the immediate vicinity of each other.

* * * * *

UNITED STATES PATENT AND TRADEMARK OFFICE
CERTIFICATE OF CORRECTION

| | | |
|---|---|---|
| PATENT NO. | : 8,951,294 B2 | |
| APPLICATION NO. | : 13/202031 | |
| DATED | : February 10, 2015 | |
| INVENTOR(S) | : Jean-Marie Gennari et al. | |

It is certified that error appears in the above-identified patent and that said Letters Patent is hereby corrected as shown below:

On the title page, please amend Item (75) to read as follows:

-- (75) Inventors: Jean-Marie Gennari, Marseilles (FR)

Herve Chataigner, Boussieres, (FR)

Jean-Marc Vital, Bordeaux, (FR)

Laurent Nogues, St Pierre-Reunion (FR)

Hugues-Pascal Mousselard, Paris (FR)

Pascal Kouyoumdjian, Nimes (FR)

Jean-Michel Tallet, Marseilles (FR)

Philippe Tisserand, Cabestany, (FR) --

Signed and Sealed this
Twenty-third Day of June, 2015

Michelle K. Lee
*Director of the United States Patent and Trademark Office*